United States Patent [19]

Guttentag

[11] 4,257,412
[45] Mar. 24, 1981

[54] MASTECTOMY BRACE

[76] Inventor: Anne Guttentag, 39 N. Main St., New Hope, Pa. 18938

[21] Appl. No.: 848,610

[22] Filed: Nov. 4, 1977

[51] Int. Cl.³ .............................................. A61F 5/30
[52] U.S. Cl. .................................................... 128/112
[58] Field of Search ............... 128/44, 78, 95, 99–104, 128/133, 134, 155, 425, 426, 427, 428, 429, 432, 447, 456, 465, 472, 478, 469, 470, 473, 482, 494; 3/36

[56] References Cited

U.S. PATENT DOCUMENTS

| 2,662,522 | 12/1953 | Muller | 128/155 |
| 2,681,059 | 6/1954 | Dietz | 128/100 |
| 2,779,943 | 2/1957 | Kelleher | 3/36 |
| 3,568,681 | 3/1971 | Comollo | 3/36 X |

FOREIGN PATENT DOCUMENTS 2279344  2/1976  France ..................................... 128/155

Primary Examiner—Robert W. Michell
Assistant Examiner—T. J. Wallen
Attorney, Agent, or Firm—Krass & Young

[57] ABSTRACT

An appliance for exerting pressure on a breast which has a surgically inserted implant including a semi-firm plate curved and contoured to form a concave section adapted to engage the upper and outer surfaces of the breast as well as the chest area surrounding these breast sides and relieved at the nipple area. A cushioning layer is secured to the concave surface of the plate which may be retained in downwardly and inwardly pressured contact with the breast either with a body strap that secures to the plate with separable fasteners and extends around the chest of the wearer or by retention of the plate within a cup of a brassiere.

6 Claims, 5 Drawing Figures

MASTECTOMY BRACE

BACKGROUND OF THE INVENTION

1. Field of the Invention.

This invention relates to an appliance for exerting forces on a breast which has undergone Mastectomy and/or contains a surgical implant to change the attitude of projection of the breast and its position.

2. Prior Art.

In the past few years techniques have been developed for surgically removing cancer of the breast without removing the entire breast. Other techniques involve removal of the breast and tumor through a single incision and then insertion of an implant through the same incision. Often the implant is inserted under the patient's pectoral muscle by extending the Mastectomy incision. This provides muscular support for the implant and its protection so that the reconstructed breast thus has a contour approximating that of the original breast.

The forces exerted by the pectoral muscle on these reconstructions can cause the implanted breast to project somewhat higher and closer to the arm than the original breast or the natural, unoperated breast. This misalignment may be sufficiently pronounced to produce a distinctly unnatural appearance which can't be effectively corrected through use of a conventional brassiere. While various forms of corrective brassieres are commercially available, the forces that they apply to the breast will not rectify this misalignment of surgically reconstructed breasts.

SUMMARY OF THE INVENTION

The present invention is broadly directed towards an appliance to be worn by women who have undergone a Mastectomy and a subsequent implant for reconstruction, to correct the attitude of projection of the reconstructed breast into compliance with that of a normal breast.

The appliance of the present invention comprises a relatively rigid plate shaped to conform to the convex surface of the new breast. One section of the concave surface is shaped to engage a section extending between the upper and outer sides of the wearer's breast and has a contour shaped to surround but not contact the nipple. An adjoining section overlies the chest of the wearer in a sector extending from the top around to the outer side of the area surrounding the breast and provides support for the breast engaging section.

The plate has a resilient undersurface formed of foamed plastic or the like so that it may be pressed against the reconstructed breast without discomfort to the wearer or injury to the skin. The plate is adapted to be retained against the upper and outer surfaces of the breast so that it presses downwardly and inwardly on the breast to force it into a more normal position. The retention for the plate may be provided by resilient straps adapted to be secured to the plate and surround the chest of the wearer. In a preferred embodiment of the invention a pair of straps are employed which attach to the upper and lower surfaces of the plate and pass over and under the natural breast of the wearer.

Alternatively, the plate may be supported within the cup of a normal brassiere to exert the required downward and inward forces on the reconstructed breast.

The appliance of the present invention is simple in construction and is not uncomfortable to wear.

Other objectives, advantages and applications of the present invention are made apparent by the following detailed description of two embodiments of the invention. The description makes reference to the accompanying drawings in which.

Figure 1:
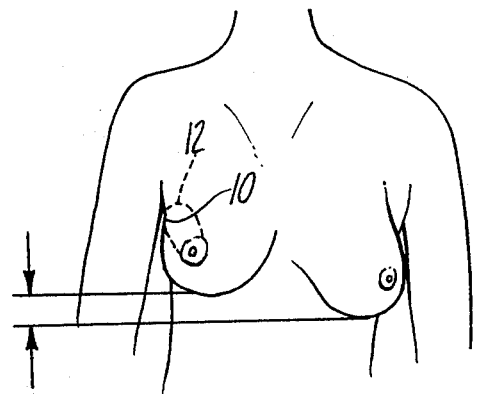
FIG. 1 is a frontal view of the breasts of a woman who has undergone a modified radical Mastectomy and the immediate surgical insertion of a corrective implant, illustrating the misalignment between the reconstructed and unreconstructed breasts.

FIG. 1 illustrates the breast area of a woman who has had a modified radical Mastectomy for the removal of a malignant tumor and the sugsequent surgical implant for the immediate reconstruction of the right breast. The surgical incision 10 is typically made outwardly from the nipple toward the pectoral muscle which extends along the outer side of the chest. A surgical implant 12, typically formed of silicone or a like inert synthetic material, is illustrated in phantom lines, within the breast, beneath the incision 10. When the implant 12 is secured beneath the pectoral muscle of the patient the resultant reconstructed breast tends to project somewhat higher and more toward the outer part of the body than the natural, uncorrected breast. This misalignment is illustrated in FIG. 1.

Figure 2:
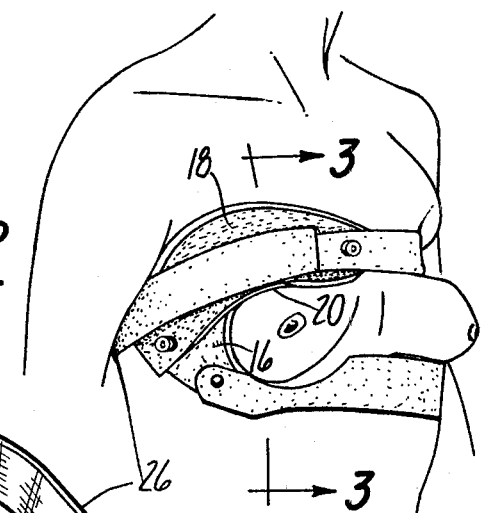
FIG. 2 is a perspective view of the breasts of the woman of FIG. 1 illustrating the patient wearing a corrective appliance formed in accordance with a first embodiment of the present invention.
Figure 4:
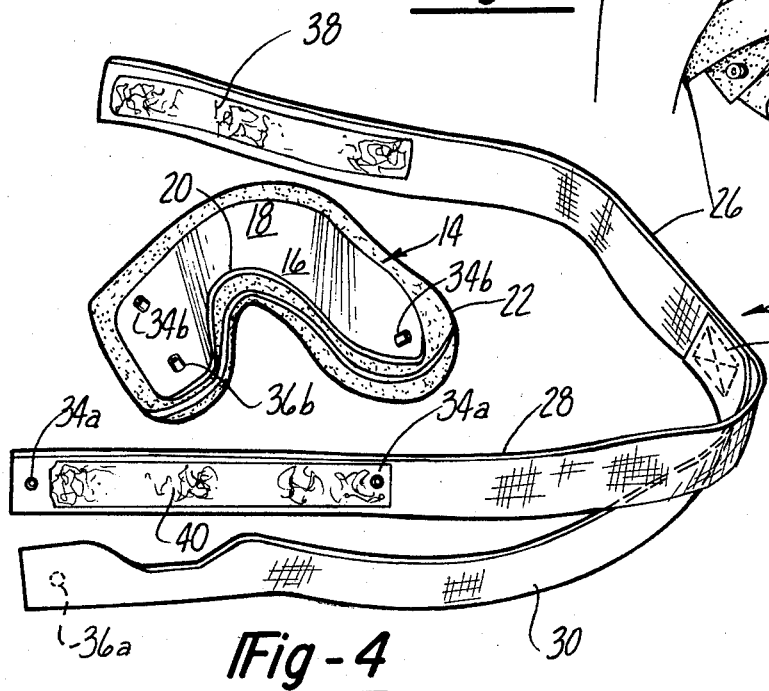
FIG. 4 is a view of the appliance worn in FIG. 2 removed from the wearer.
Figure 3:
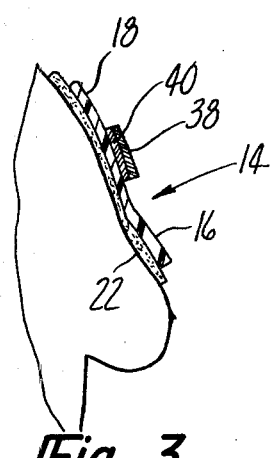
FIG. 3 is a sectional view through the breast and appliance illustrated in FIG. 2.
Figure 5:
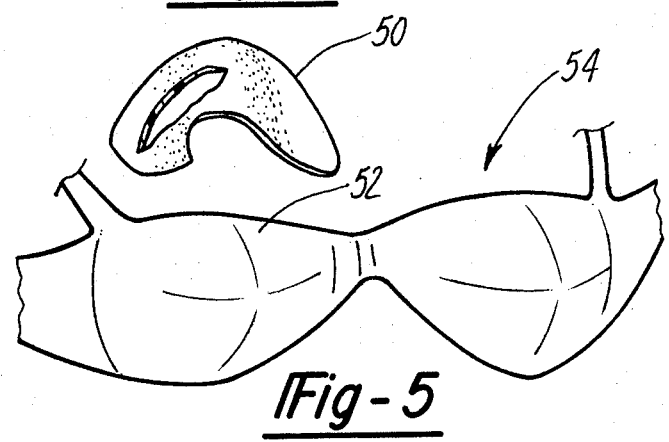
FIG. 5 is an illustration of an alternative embodiment of the present invention, adapted to be retained in place by a conventional brassiere and shown in exploded position relative to a brassiere.

A preferred form of an appliance for correcting the misalignment illustrated in FIG. 1 is shown in FIGS. 2, 3, and 4. It broadly comprises a plate, generally indicated at 14, formed of a semi-rigid plastic such as fiberglass reinforced polyester resin. The plate 14 has one area, 16, that is generally contoured to overlie the upper and outer sides of the breast of the wearer, and another area 18 that is adapted to overlie the chest of the wearer surrounding the upper and outer sides of the breast. The underside of the plate 14 is concavely curved to conform to both the covered section of the breast and the surrounding chest section. The margins of the plate in the breast surrounding areas 16 are relieved as at 20 so as to prevent contact with the nipple.

A resilient pad 22 of foamed plastic or the like, having a marginal edge slightly larger than that of the plate 14, is secured to the concave underside of the plate so as to be sandwiched between the plate and the breast and cushion the breast.

The plate 14 and the underlying pads 22 may be custom designed to fit individual cases or may be made commercially available in a series of standard sizes and shapes.

The preferred embodiment of plate 14 is secured to the breast of the wearer employing a chest surrounding strap, generally indicated at 24. The strap is preferrably formed of an elastic material in a Y-shaped configuration including one main leg 26 and a divided pair of sections 28 and 30 which secure to one end of the section 26 at a joint 32. The upper engaging section 28 has a pair of snap fasteners 34a formed at spaced points near its end, adapted to engage a pair of complementary snap fasteners 34b formed on the upper sides of the plate 14. Similarly, the lower strap section 30 has a female snap fastener 36a formed on its end, adapted to releasably engage a complementary fastener 36b formed on the bottom extremity of the plate 14 on its outer side.

The strap section 26 has a hook-and-eye fastener strip 38, of the type marketed under the Trademark VELCRO, affixed to its underside and the strap section 28 has a complementary hook-and-eye fastener strip 40 secured to its upper side. In use, in the manner illustrated in FIG. 2, the fasteners 34 and 36 on the strap are affixed to the complementary fasteners on the plates 14 and the strap section 26 is wrapped around the chest of the wearer and the hook-and-eye fastener section 38 is secured to the section 40. The tension is adjested through use of the adjustable fastener strips 38 and 40 to provide a comfortable yet firm pressure which forces the section 16 of the plate downwardly against the upper side of the breast, and inwardly against the outer side of the breast. This pressure forces the sugically corrected breast downwardly and inwardly into the same attitude as the natural breast.

An alternative form of the invention is illustrated in FIG. 4. A plate 50 having a contour much like the plate 14, and a thin resilient coating on its concave underside, is adapted to be inserted within the cup section 52 of a conventional brassiere, generally indicated at 54. The plate 50 is inserted under the cup 52 so that it engages the upper and outer surfaces of the breast. The brassiere straps are adjusted to produce the necessary forces on the plate 50 to force the surgically corrected breast into the desired alignment.

I claim:

1. An appliance adapted to alter the attitude of projection of a breast in a downward and inward manner, comprising: a substantially rigid, generally U-shaped plate having a first section formed with an edge contoured to conform to the upper surface of the breast and a second section formed with an edge contoured to conform to the outer surface of the breast, the two sections being joined by a concave edge adapted to adjoin and partially surround the nipple area, and an adjoining section contoured to extend over the chest areas on the upper and outer side of the breast; and an elongated strip having mating separable fastener means on its opposed ends and means formed on one end for joinder to said first section of the plate, and a second strip having one end secured to a mid-point of the first strip and means on its other end for joinder to said second section of the plate, whereby the plate may be secured in pressured contact with the upper and outer surfaces of the breast to produce downward and inwardly directed forces on the breast by wrapping the first strip about the chest of the wearer and joining its ends with said separable fasteners.

2. The appliance of claim 1 including a resilient covering attached to the side of the plate adapted to engage the breast and chest of the wearer.

3. The appliance of claim 1 wherein said means for retaining the plate in pressured contact with the upper and outer surfaces of the breast includes a strap affixed to the plate and adapted to surround the chest of the wearer.

4. The appliance of claim 3 in which the strap includes a pair of sections, one of which extends over the adjacent, unengaged breast of the wearer, and the other which passes over the last said breast.

5. The appliance of claim 1 in which said means for retaining the plate comprises a brassiere having a cup adapted to surround the breast and the plate is disposed between the cup and the breast.

6. The appliance of claim 1 wherein the plate is formed of plastic.

* * * * *